US009096831B2

(12) United States Patent
Chan et al.

(10) Patent No.: US 9,096,831 B2
(45) Date of Patent: Aug. 4, 2015

(54) METHODS TO ENHANCE CELL MIGRATION AND ENGRAFTMENT

(75) Inventors: Barbara Pui Chan, Hong Kong (HK); Hoi Ling Wong, Hong Kong (HK); Mei Yi Wong, Hong Kong (HK); Godfrey Chi-Fung Chan, Hong Kong (HK); Zhen Fan Yang, Shanghai (CN)

(73) Assignee: Versitech Limited, Hong Kong (HK)

( * ) Notice: Subject to any disclaimer, the term of this patent is extended or adjusted under 35 U.S.C. 154(b) by 419 days.

(21) Appl. No.: 13/159,835

(22) Filed: Jun. 14, 2011

(65) Prior Publication Data
US 2012/0148537 A1  Jun. 14, 2012

Related U.S. Application Data

(63) Continuation-in-part of application No. 11/750,863, filed on May 18, 2007, now Pat. No. 8,679,809.

(60) Provisional application No. 60/801,975, filed on May 19, 2006, provisional application No. 61/354,871, filed on Jun. 15, 2010.

(51) Int. Cl.
C12N 11/04 (2006.01)
C12N 5/0775 (2010.01)
(Continued)

(52) U.S. Cl.
CPC ............ *C12N 5/0663* (2013.01); *A61K 9/1635* (2013.01); *A61K 35/28* (2013.01); *C12N 11/04* (2013.01); *A61K 2035/128* (2013.01); *C12N 5/0606* (2013.01); *C12N 5/0665* (2013.01); *C12N 5/0666* (2013.01); *C12N 5/0696* (2013.01); *C12N 2533/50* (2013.01); *C12N 2533/54* (2013.01); *C12N 2533/56* (2013.01); *C12N 2533/80* (2013.01); *C12N 2533/90* (2013.01)

(58) Field of Classification Search
CPC .. C12N 5/0606; C12N 5/0663; C12N 5/0666; C12N 5/0765; C12N 2533/54; C12N 5/0012; C12N 5/0665; C12N 5/0696; C12N 5/0675; C12N 11/04; C12N 2533/50; A61K 35/28; A61K 2035/128
USPC .......................................... 435/325; 424/93.7
See application file for complete search history.

(56) References Cited

U.S. PATENT DOCUMENTS

2007/0292514 A1*  12/2007  Chan Pui et al. ............. 424/484

FOREIGN PATENT DOCUMENTS

WO        WO 00/06704        *  2/2000   ............... C12N 5/08

OTHER PUBLICATIONS

Lee et al, Blood, 2006 (e pub Nov. 8, 2005) vol. 107, pp. 2153-2161.*
(Continued)

*Primary Examiner* — Allison Fox
(74) *Attorney, Agent, or Firm* — Pabst Patent Group LLP

(57) ABSTRACT

A method is provided to functionally select cells with enhanced characteristics relevant to cell engraftment, including both spontaneous migration and directional migration towards specific chemo-attractants. The cells are preferably undifferentiated cells, such as mesenchymal stem cells. The method involves entrapping or encapsulating the cells in a biomaterial barrier, optionally inducing cell migration, and selecting cells that migrated through the barrier. The cells selected by this method have better migratory activities and enhanced in vivo engraftment to injured tissues when they are supplemented systemically.

25 Claims, 8 Drawing Sheets

(51) Int. Cl.
*A61K 9/16* (2006.01)
*A61K 35/28* (2015.01)
*C12N 5/0735* (2010.01)
*C12N 5/074* (2010.01)
*A61K 35/12* (2015.01)

(56) References Cited

OTHER PUBLICATIONS

Barrilleaux, et al., "Review: ex vivo engineering of living tissues with adult stem cells", Tissue Eng., 12(11):3007-19 (2006).
Bhakta, et al., "The surface adhesion molecule CXCR4 stimulates mesenchymal stem cell migration to stromal cell-derived factor-1 in vitro but does not decrease apoptosis under serum deprivation", Cardiovasc Revasc Med., 7(1):19-24 (2006).
Chamberlain, et al. "Concise review: mesenchymal stem cells: their phenotype, differentiation capacity, immunological features, and potential for homing", Stem Cells., 25(11):2739-49 (2007).
Chan, et al., "Self-assembled collagen-human mesenchymal stem cell microspheres for regenerative medicine", Biomaterials, 28:4652-4666 (2007).
Chavakis, et al., "Homing and engraftment of progenitor cells: a prerequisite for cell therapy", J Mol Cell Cardiol.,45(4):514-22 (2008).
Chen, et al., "Improvement of cardiac function after transplantation of autologous bone marrow mesenchymal stem cells in patients with acute myocardial infarction", Chin Med J (Engl)., 117(10):1443-8 (2004).
Colter, et al., "Identification of a subpopulation of rapidly self-renewing and multipotential adult stem cells in colonies of human marrow stromal cells",PNAS, 98(14):7841-5 (2001).
Dar, et al., "Mutual, reciprocal SDF-1/CXCR4 interactions between hematopoietic and bone marrow stromal cells regulate human stem cell migration and development in NOD/SCID chimeric mice", Exp Hematol., 34(8):967-75 (2006).
Dar, et al., "Chemokine receptor CXCR4-dependent internalization and resecretion of functional chemokine SDF-1 by bone marrow endothelial and stromal cells", Nat Immunol., 6(10):1038-4 (2005).
Deschaseaux, et al., "Direct selection of human bone marrow mesenchymal stem cells using an anti-CD49a antibody reveals their CD45med,low phenotype", Br J Haematol., 122(3):506-17 (2003).
Digirolamo, et al., "Propagation and senescence of human marrow stromal cells in culture: a simple colony-forming assay identifies samples with the greatest potential to propagate and differentiate", Br J Haematol., 107(2):275-81 (1999).
Helm, et al., "Future uses of mesenchymal stem cells in spine surgery", Neurosurg Focus., 15;19(6):E13 (2005).
Honczarenko, et al., "Human bone marrow stromal cells express a distinct set of biologically functional chemokine receptors", Stem Cells, 24(4):1030-41 (2006).
Horwitz, et al., "Transplantability and therapeutic effects of bone marrow-derived mesenchymal cells in children with osteogenesis imperfecta", Nat Med., 5(3):309-13 (1999).
Pittenger, et al., "Mesenchymal stem cells and their potential as cardiac therapeutics", Circ Res., 95(1):9-20 (2004).
Pittrnger, et al., "Multilineage potential of adult human mesenchymal stem cells", Science , 2;284(5411):143-7 (1999).
Ponte, et al., "The in vitro migration capacity of human bone marrow mesenchymal stem cells: comparison of chemokine and growth factor chemotactic activities", Stem Cells., 25(7):1737-45 (2007).
Price, et al., "Intravenous mesenchymal stem cell therapy early after reperfused acute myocardial infarction improves left ventricular function and alters electrophysiologic properties", Int J Cardiol., 111(2):231-9 (2006).
Ries, et al., "MMP-2, MT1-MMP, and TIMP-2 are essential for the invasive capacity of human mesenchymal stem cells: differential regulation by inflammatory cytokines", Blood, 109(9):4055-63 (2007).
Seeger et al., "Cell-enhancement strategies for the treatment of ischemic heart disease", Nat Clin Pract Cardiovasc Med., 4 Suppl 1:S110-13 (2007).
Shi, et al., "Regulation of CXCR4 expression in human mesenchymal stem cells by cytokine treatment: role in homing efficiency in NOD/SCID mice", ,Haematologica. 92(7):897-904 (2007).
Short, et al., "Mesenchymal stem cells", Arch Med Res., 34(6):565-71 (2003).
Simmons, et al., "Identification of stromal cell precursors in human bone marrow by a novel monoclonal antibody, STRO-1", Blood, 78(1):55-62 (1991).
Son, et al., "Migration of bone marrow and cord blood mesenchymal stem cells in vitro is regulated by stromal-derived factor-1-CXCR4 and hepatocyte growth factor-c-met axes and involves matrix metalloproteinases", Stem Cells, 24(5):1254-64 (2006).
Sordi, et al., "Bone marrow mesenchymal stem cells express a restricted set of functionally active chemokine receptors capable of promoting migration to pancreatic islets", Blood, 106(2):419-27 (2005).
Tondreau, et al., "Isolation of BM mesenchymal stem cells by plastic adhesion or negative selection: phenotype, proliferation kinetics and differentiation potential", Cytotherapy., 6(4):372-9 (2004).
Wang, et al., "Intravenous infusion of bone marrow mesenchymal stem cells improves myocardial function in a rat model of myocardial ischemia", Crit Care Med., 35(11):2587-93 (2007).
Yamaguchi, et al., "Stromal cell-derived factor-1 effects on ex vivo expanded endothelial progenitor cell recruitment for ischemic neovascularization", Circulation., 107(9):1322-8 (2003).

\* cited by examiner

METHODS TO ENHANCE CELL MIGRATION AND ENGRAFTMENT

CROSS REFERENCE TO RELATED APPLICATIONS

This application is a continuation-in-part of co-pending U.S. patent application Ser. No. 11/750,863, filed May 18, 2007, which claims benefit of and priority to U.S. Provisional Patent Application No. 60/801,975 filed May 19, 2006. This application claims benefit of U.S. Provisional Patent Application No. 61/354,871, filed Jun. 15, 2010. All of the above are hereby incorporated by reference in their entirety.

FIELD OF THE INVENTION

The invention is generally related to the field of cell engraftment, more particularly to methods and compositions for enhancing both spontaneous migration and directional migration of transplanted cell populations.

BACKGROUND OF THE INVENTION

Cell-based therapy, particularly using undifferentiated cells, e.g., multipotent or pluripotent cells stem cells, presents a promising approach for regenerative medicine and tissue engineering (Short et al. *Arch Med. Res.* 2003 34(6):565-71, Barrilleaux et al. *Tissue Eng.* 2006 12(11):3007-19). In particular, bone marrow mesenchymal stem cells (MSCs), or stromal stem cells, have been shown to be beneficial in regenerating tissues of musculoskeletal (Horwitz et al. *Nat. Med.* 1999 March; 5(3):309-13), cardiovascular (Pittenger et al. *Circ Res.* 2004 95(1):9-20; Chen et al. *Chin Med J* (*Engl*). 2004 117(10):1443-8. Erratum in: *Chin Med J* (*Engl*). 2005 118(1):88; Price et al. *Int J Cardiol.* 2006 111(2):231-9; Wang et al. *Crit. Care Med.* 2007 35(11):2587-93) and neurological (Helm et al. *Neurosurg Focus.* 2005 15; 19(6):E13) systems. This is because of their relatively safety and easy accessibility from the donor, genetic stability, and the ability of self-renewal and differentiating into multiple lineages of cells (Pittenger et al. *Science* 1999 2; 284(5411):143-7; Pittenger et al. *Circ Res.* 2004 95(1):9-20). They also have the unique immunologically privileged status which can ignore the Human Leukocyte Antigen histocompatibility barrier (Pittenger et al. *Circ Res.* 2004 95(1):9-20). It is also more socially and ethically acceptable to use MSCs than embryonic stem cells.

Despite the great potential of MSC-based therapies, the functional outcomes of existing MSC therapies have not been satisfactory, at least partly due to the extremely poor engraftment rate (usually <1-2%) of MSCs at the target tissues such as hearts in the treatment of myocardial infarction (Price et al. *Int J. Cardiol.* 2006 111(2):231-9; Wang et al. *Crit. Care Med.* 2007 35(11):2587-93) and bones in the treatment of osteogenic imperfecta (Horwitz et al. *Nat. Med.* 1999 5(3):309-13) upon systemic injection. It is generally believed that the outcomes of MSC therapies can be further enhanced if the engraftment efficiency of human MSCs can be improved. As a result, strategies aimed to enhance the engraftment rate are important to improving the efficacy of MSCs-based therapies.

Local injection of MSCs with and without carriers is able to improve engraftment in the target tissue such as heart and intervertebral disc, but the extent of improvement is less than 5%, which is too low to generate a significant impact. Moreover, the invasiveness associated with the open surgery-based injection into inner organs such as heart and spine, and the inapplicability of local injection in diseases where multiple tissues are involved, such as osteogenic imperfecta and muscle dystrophy, prevents this approach from being widely used in regenerative medicine. Currently, no effective method exists to improve the engraftment rate of systemically supplemented MSCs.

Stem cell engraftment, sometimes used interchangeably with stem cell homing, describes the process of directing undifferentiated cells, such as MSCs, to migrate from the peripheral blood into the damaged tissues (Chamberlain et al. *Stem Cells.* 2007 25(11):2739-49; Chavakis et al. *J Mol Cell Cardiol.* 2008 45(4):514-22). The detailed mechanisms of stem cell engraftment are still unclear but directional movement of stem cells towards gradients of chemoattractants and cytokines induced by tissue injuries is known to play an important role (Ponte et al. *Stem Cells.* 2007 25(7):1737-45; Sordi et al. *Blood.* 2005 106(2):419-27; Son et al. *Stem Cells.* 2006 24(5):1254-64; Honczarenko et al. *Stem Cells.* 2006 24(4):1030-41; Ries et al. *Blood.* 2007 109(9):4055-63). Among all chemoattractant and receptor pairs, SDF-1 and its specific receptor CXCR4 have been shown to be most important in regulating the migration of hMSCs [Ponte et al. *Stem Cells.* 2007 25(7):1737-45; Dar et al. *Nat. Immunol.* 2005 6(10):1038-4; Dar et al. *Exp Hematol.* 2006 34(8):967-75; Honczarenko et al. *Stem Cells.* 2006 24(4):1030-41).

Several attempts have been made recently to enhance the responsiveness of MSCs towards specific chemoattractants. In particular, MSCs have been treated with chemoattractants such as SDF-1 (Shi et al. *Haematologica.* 2007 July; 92(7): 897-904; Ponte et al. *Stem Cells.* 2007 25(7):1737-45), or virally transduced with chemoattractant receptor genes such as CXCR4 (Bhakta et al. *Cardiovasc Revasc Med.* 2006 7(1): 19-24). Both methods upregulate the expression of the chemoattractant receptor on MSCs. A few other approaches include viral transduction of MSCs with anti-apoptotic genes such as Akt and telomerase to promote MSC survival (Seeger et al. *Nat Clin Pract Cardiovasc Med.* 2007 4 Suppl 1:S110-3) and extrinsic supplementation of chemoattractants such as SDF-1 at the injured target tissues to augment the chemoattractant signal for MSC recruitment at the injury site (Yamaguchi et al. *Circulation.* 2003 107(9):1322-8). Nevertheless, these approaches also have significant drawbacks such as the long term uncertainty of genetically manipulated cells, the safety issue of virally transduced cells and the poor cost-effectiveness of in vivo supplementation of chemoattractants. More importantly, none of these attempts address the heterogeneity problem of MSCs.

It is therefore an object of the invention to provide methods and compositions to promote or enhance migration, engraftment, or a combination thereof of transplanted cells, such as MSCs.

SUMMARY OF THE INVENTION

A method to process undifferentiated cells for engraftment, such as MSCs, by functionally selecting subpopulations of undifferentiated cells with better migratory activity has been developed. The method enhances both spontaneous migration and directional migration of the cells towards specific chemo-attractants. The method also provides a means to enhance the in vivo engraftment rate of undifferentiated cells during tissue repair and regeneration.

In preferred embodiments, the method involves entrapping or encapsulating undifferentiated cells in a biomaterial barrier, optionally inducing the cells to migrate, and selecting cells that migrate through the barrier. The selected cells have better characteristics such as in vitro migratory activities and in vivo engraftment rate to injured tissues when they are supplemented systemically. The cells can be undifferentiated cells, such as multipotent or pluripotent stem cells. In preferred embodiments, the cells are mesenchymal stem cells (MSCs), such as human MSCs (hMSCs).

DETAILED DESCRIPTION OF THE INVENTION

Figure 1:
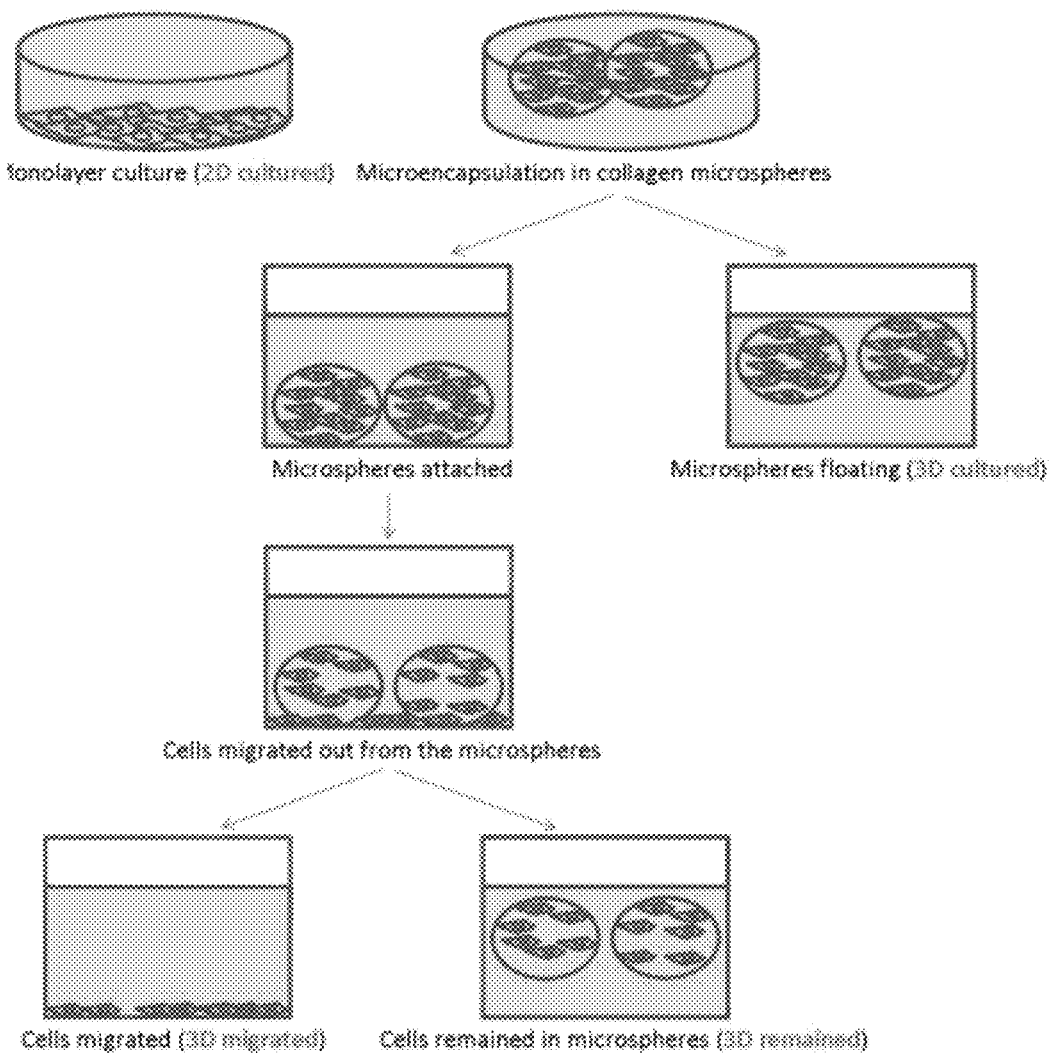
FIG. 1 is a flow chart illustrating the disclosed method of selecting subpopulations of undifferentiated cells with better migratory activity.

A common challenge in cell-based therapies using undifferentiated stem cells, such as human mesenchymal stem cell (hMSC), is limited engraftment efficiency. One of the key steps governing the engraftment rate is the ability of stem cells, including but not limited to pluripotent or multipotent cells, to migrate to the targeted injury sites. As a result, strategies for enhancing the migratory activities are important for development cell engraftment therapies. Undifferentiated cell populations, such as hMSCs, generally contain heterogeneous mixtures of multiple cell types, which differ in morphology, phenotype, and functional properties including migratory activities. A method of selecting undifferentiated stem cells, such as hMSCs, with better migratory activities using a biomaterial barrier, such as collagen, is described.

In one embodiment, hMSCs were subjected to a self-selection process via microencapsulation in a collagen barrier and induced to migrate out from this barrier. The hMSC subpopulation that migrates out of the barrier has a significantly better migratory response, both spontaneously towards serum free medium and directionally towards well-known chemoattractants, as compared to other subpopulations, including those remaining inside the collagen barrier and those in traditional 2D cultures. Moreover, the selection of hMSCs by this method is positively associated with the concentration of the collagen barrier and the cell density.

I. DEFINITIONS

As used herein, "cell engraftment" or "cell homing" refers to the process by which cells, such as stem cells, that are transplanted into a subject incorporate into tissues of the subject.

As used herein, "crude preparation of cells" refers to a heterogeneous population of cells isolated from a tissue source prior to any selection process.

As used herein, "inducing cells to migrate" refers to the use of conditions that are suitable for, or promote cell migration. The conditions include physical, biological, and chemical stimuli that promote migration of cells, including, but not limited to, culture on a substratum and the use of serum or specific chemokines in the culture medium.

As used herein, "spontaneous migration" refers to the migration of cells in the absence of specific chemoattractants.

As used herein, "directional migration" refers to the migration of cells towards chemoattractants.

As used herein, "stem cell" refers generally to an undifferentiated cell regardless of source, and includes multipotent cells or pluripotent cells. Stem cells include de-differentiated cells, embryonic stem cells, mesenchymal stem cells, and induced pluripotent stem cells. Stem cells can be embryonic or adult stem cells.

As used herein, "progenitor cell" refers generally to unipotent or oligopotent cells that do not replicate indefinitely.

As used herein, "totipotency" refers to a single undifferentiated cell with the ability to divide and produce all the differentiated cells in an organism, including extraembryonic tissues.

As used herein, "pluripotency" refers to a single undifferentiated cell with the ability to differentiate into cells of any of the three germ layers: endoderm (e.g., interior stomach lining, gastrointestinal tract, the lungs), mesoderm (e.g., muscle, bone, blood, urogenital), or ectoderm (e.g., epidermal tissues and nervous system). Pluripotent cells cannot develop into a fetal or adult animal because they lack the potential to contribute to extraembryonic tissue, such as the placenta.

As used herein, "multipotent" refers to a single undifferentiated cell with the ability to differentiate into multiple cell lineages but not to cells of all three germ layers.

As used herein, "oligopotent" refers to a single undifferentiated cell with the ability to differentiate into a few cell types.

As used herein, "subject" refers to any individual who is the target of administration. The subject can be a vertebrate, for example, a mammal. Thus, the subject can be a human. The term does not denote a particular age or sex. A patient refers to a subject afflicted with a disease or disorder. The term "patient" includes human and veterinary subjects.

II. METHODS OF MODIFYING MSC MIGRATION

A representative method for modifying stem cell migration includes functionally selecting cells with enhanced characteristics relevant to cell engraftment, such as migratory activities. The method involves entrapping cells, such as a crude cell pellet, in a biomaterial barrier or a gradient of one or more biomaterial barriers. The cells are obtained from conventional processing methods such as adhesion selection or flow cytometry sorting. Cells for use in the selection method can be undifferentiated or mature differentiated cells that are suitable for cell engraftment. Preferred cells are undifferentiated stem cells or progenitor cells. The specific source of undifferentiated cells can be selected based on the target tissue for engraftment. For example, mesenchymal stem cells (MSCs) are particularly suitable for musculoskeletal, cardiovascular and neurological systems. MSCs can be obtained from various sources, including, but not limited to, bone marrow, adipose tissue, umbilical cord, and blood. In addition, MSCs can be derived from pluripotent stem cells, such as induced pluripotent stem (iPS) cells and embryonic stem (ES) cells.

The biomaterial barrier used should be able to entrap or encapsulate the cells under physiologically relevant conditions yet allow the entrapped cells to penetrate or invade and then migrate through or transmigrate under certain conditions. As used herein, "functional" means the ability to migrate through a barrier. As a result, many biomaterials can be used, including but are not limited to extracellular matrix materials ("ECM") such as collagen, fibrin, Matrigel™, self-assembled peptides, and hyaluronic acid. Collagen is a preferred example. Moreover, the barrier can be in any form, including, but not limited to, microspheres, block gel, cylindrical shaped, patch, and thin film.

The barrier can be a homogenous barrier with a homogeneous fiber density or barrier capacity, or a gradient barrier of increasing fiber density or barrier capacity, or any combination with other material barrier selectively allowing migration of different cells. Numerous fabrication technologies such as reconstitution, self-assembly, nested self-assembly, 3D printing, photopolymerization, and electrospinning can be used to form the barrier.

The following is an exemplary description for selecting hMSCs for cell engraftment using collagen microencapsulation. It is understood that the following steps can be adapted to other cells and biomaterials.

A. Trapping Crude hMSCs in a Biomaterial Barrier

A microencapsulation technique is used to entrap hMSCs within a biomaterial barrier in a three dimensional configuration. Crude hMSCs (referred to as two dimensional (2D) cultured) are obtained from various sources including, but not limited to, bone marrow, cord blood, and placenta. The hMSCs are obtained at a concentration of $1 \times 10^3$ cells/ml to $1 \times 10^6$ cells/ml, preferably $1 \times 10^4$ cells/ml.

In some embodiments, the hMSCs are cultured 3 days to 14 days prior to microencapsulation. For example, the hMSCs can be cultured in a full medium containing Dulbecco's modified Eagle's medium-low glucose (DMEM-LG), 10% fetal bovine serum (FBS), 100 U/ml penicillin, 100 mg/ml streptomycin and 1% glutamax, or full medium with lower % of FBS such as 5%, or other medium able to support the growth of MSCs. The hMSCs are preferably cultured from about 50% to about 99% confluence, more preferably 80% confluence. For example, the hMSCs can be cultured for about 3 days to about 14 days, including about 6 days. Once the hMSCs reach the desired confluence, the cells are enzyme digested (e.g., trypsinized) and suspended for subsequent microencapsulation.

In preferred embodiments, the biomaterial barrier is collagen, which is mixed with the hMSC suspension. For example, rat-tail collagen type 1 solution can be neutralized by 1N NaOH and mixed with the hMSC suspension. The final collagen concentration is preferably about 0.5 mg/ml and the final cell density is about $1 \times 10^3$ cells/ml to $1 \times 10^7$ cells/ml, preferably about $1 \times 10^5$ cells/ml.

The cell-collagen mixture is dispensed as structures, including but not limited to, patches, droplets, thin layers, and blocks, onto a collection platform with a non-adherent surface. The structures are incubated at 37° C. for at least 1 hour to allow for reconstitution into solid structures, which is then collected into a container, such as a Petri dish, supplemented with full medium.

B. Induction of hMSC Migration Through the Barrier

Since hMSCs are adherent cells, they prefer a substratum for attachment. By providing a substratum, such as a rigid substratum of culture dish or soft collagen gel matrix, to the MSC-encapsulated collagen barrier, some hMSCs are able to migrate out through the collagen fibrous meshwork with different densities or concentrations. The method can also include a step of allowing interactions of the entrapped cells with the biomaterial barrier for certain period of time in suspension or free floating cultures prior to culture on a substratum. The duration of this culture period ranges from 0 hours to 14 days, preferably 3 to 4 days. This is to allow the cells to adapt to the 3D matrix environment and the soft matrix barrier of the microspheres to contract to an equilibrium status.

These encapsulated cells are then transferred into a tissue culture dish with an adherent surface or a collagen gel cushion. A minimal amount of culture medium can be supplemented to prevent "free-floating" of the structures after attaching to the substratum of the tissue culture dish for a period of time sufficient for the structures to attach to the substratum provided, ranging from 0.5 hour to 10 hours, preferably 0.5 hour. Full medium is carefully supplemented afterwards so as not to mechanically disturb the attached structures. After about three days, hMSCs that have migrated out from these structures to the adherent substratum of the tissue culture dish are collected. In some embodiments, these collected cells are functionally selected hMSCs. In other embodiments, the collected cells are cultured for another period of time for expansion, ranging from one day to 14 days, preferably three days, then collected as functionally selected hMSCs.

Optionally, the barriers are detached from the substratum by mechanical means such as agitation or flushing with medium. The detached barriers can be plated again to start another round of inducing the entrapped cells to migrate out.

The functionally selected hMSCs can also be enriched by methods such as subcultures or clonal selection, before use in cell engraftment.

A kit containing materials, tools and protocols for the functional selection of MSC subpopulations with better migratory activities and therefore engraftment can be prepared for use in the method described above, and as demonstrated in the following examples. The associated product can be a kit for cell processing. The kit includes two or more of a device for collecting the tissue source, a device to do initial selection of MSCs, devices and reagents to do the encapsulation and the induction steps, devices to enable migration selection, devices and reagents for collection of the functionally selected cell subpopulations, and devices for systemic injection or implantation or delivery of the processed cells. The components of the kit are packaged in a container, typically a container suitable for shipping.

III. SELECTED MSC POPULATIONS

MSCs are present in extremely low percentages (<0.1%) in bone marrow and other sources such as adipose tissues. They can be separated from haematopoietic stem cells and other cells by negative immunoselection for haematopoietic and endothelial markers such as CD34 and CD45 (Deschaseaux et al. *Br J Haematol.* 2003 122(3):506-17), positive immunoselection for Stro-1 (Simmons et al. *Blood.* 1991 Jul. 1; 78(1):55-62), or adhesion selection based on their ability to adhere to the culture substratum (Tondreau et al. *Cytotherapy.* 2004 6(4):372-9; Pittenger et al. *Circ Res.* 2004 95(1):9-20). Nevertheless, MSCs isolated by these methods are still a heterogeneous mixture of multiple types, which differ in morphology, phenotype, genotype and functional properties including migratory activities (Colter et al. *Proc Natl Acad Sci USA.* 2001 98(14):7841-5; Sordi et al. *Blood.* 2005 106 (2):419-27; Digirolamo et al. *Br J Haematol.* 1999 107(2): 275-81). Therefore, transplanting MSC as a crude mixture results in low engraftment.

The cells obtained using the method described above are enriched subpopulations of MSCs with better intrinsic migratory activities both spontaneously and directionally towards chemokines secreted into the circulation during tissue injuries, such as Fractalkine and SDF-1. More importantly, the selected MSC subpopulations have a better engraftment rate to the injured tissue such as liver, heart, and bone, when injected systemically. This may be due to better migratory activities alone, or in combination with other activities such as better transmigration through the endothelial barrier, better survival at the hostile environment of the tissue defect, and better survival and functional remodeling at the defect site. The functionally selected stem cells have unaltered, if not improved, self-renewal capacity and multiple differentiating potential.

IV. METHODS OF USE

Cell populations, e.g., hMSCs, functionally selected by the disclosed method are useful in treating tissue injuries and in regenerative medicine and tissue engineering. For example, in cell based regenerative medicine for tissue injuries, the functionally selected cells can be injected to the blood stream of individuals with defective tissues. Functionally selected cells, such as hMSCs, have enhanced engraftment in tissue defects and therefore improve the functional outcome of cell-based therapy.

The present invention will be further understood by reference to the following non-limiting examples.

EXAMPLES

Example 1

Microencapsulation of hMSCs Using Collagen Barrier

Materials and Methods

Bone marrow aspirates were collected from two healthy bone marrow donors (Subject 1 and 2) with informed consents. hMSCs were cultured in full medium consisting of Dulbecco's modified Eagle's medium-low glucose (DMEM-LG), 10% fetal bovine serum (FBS), 100 U/ml penicillin, 100 mg/ml streptomycin and 1% GlutaMax™ at 37° C. with 5% $CO_2$. Cells at passage 4 were subcultured as traditional 2D (monolayer) cultures. The initial cell seeding density of traditional 2D culture was $6.25 \times 10^4$ per 100 mm tissue culture dish.

After trypsinization, cells at passage 5 were labeled "2D cultured cells." Some of these cells were used for subsequent microencapsulation. hMSCs were trypsinized using 0.05% Trypsin-EDTA (Gibco).

Cells were microencapsulated in a collagen barrier as described by Chan, et al. Biomaterials 28 (2007) 4652-4666. Rat-tail collagen type 1 solution (BD Biosciences) was neutralized by 1N NaOH and diluted to a final concentration of 0.5, 1, 2 or 3 mg/ml in the presence of hMSCs in DMEM-LG. The final cell density was $1 \times 10^5$ cells/ml or $5 \times 10^5$ cells/ml. The cell-collagen mixture was dispensed as 2.5 μl droplets onto a collection platform with non-adherent surface. The microdroplets were incubated at 37° C. for 1 hour to allow for reconstitution into solid microspheres, which were then collected into 90 mm Petri dish supplemented with full medium.

Two hundred and fifty microspheres were collected into each Petri dish such that the total cell number of each Petri dish was equivalent to the initial cell seeding density of traditional 2D culture for comparison. Images of samples under optical microscope (Leica) were taken at different time points to evaluate the size and morphology of the hMSCs-collagen microspheres. The hMSCs-collagen microspheres were cultured at free-floating condition in a 90 mm Petri dish supplemented with full medium for 3 days. Some of the microspheres were then digested using collagenase (200 unit/ml; Sigma) followed by 0.05% Trypsin-EDTA to further separate the cells into single cell suspension. The cells collected were labeled as "3D cultured cells."

The other microspheres were transferred from Petri dish into tissue culture dish and were attached to the substratum of the tissue culture dish supplemented with full medium for 3 days to allow the hMSCs entrapped inside the collagen matrix to migrate out to the surrounding substratum. After that, the microspheres were detached from the substratum and digested using collagenase followed by 0.05% Trypsin-EDTA to collect cells remaining within the microspheres. These cells were labeled as "3D remained cells."

Cells that migrated out from the collagen microspheres were further cultured for 3 days, trypsinized using 0.05% Trypsin-EDTA and labeled as "3D migrated cells."

Some of the 3D migrated cells were further subcultured in full medium and the cells collected afterwards were labeled as "Subcultured cells."

Results

FIG. 1 shows the overview of all treatments and labeling of different cell subpopulations. hMSCs were entrapped in a dense collagen fiber meshwork barrier. Cells were entrapped but not migrated out when cultured free floating or in suspension, while some cells migrated out when the barriers were attached or plated to a substratum. The 3D migrated cells had a more homogenously smaller cell morphology as compared to the 2D cultured cells.

Example 2

Transwell Migratory Activities of Different hMSC Subpopulations

Materials and Methods

Serum free medium alone or in the presence of either 10 ng/ml Fractalkine ($CX_3CL1$; Peprotech) or 50 ng/ml SDF-1β (CXCL12; Peprotech) in a total volume of 800 μl was added into the lower chamber of a 24-well plate transwell (BD Biosciences). A cell culture insert 8 μm pore size (BD Falcon™ Cell Culture Inserts, catalog #353097) was gently placed into the well. An aliquot of $5 \times 10^4$ hMSCs collected from the different treatment groups of Example 1: 2D cultured cells, 3D cultured cells, 3D remained cells, 3D migrated cells or Subcultured cells, was suspended in 250 μl serum free medium and added into the insert in the upper chamber of the transwell. The cells were then incubated at 37° C. with 5% $CO_2$ for 16 hours.

The insert was then removed from the well and the non-migrating cells from the upper side of the membrane were removed gently using a cotton bud. The lower side of the membrane was fixed with methanol followed by Diff Quik solution I and II (LabAids) for 6 minutes each. Ten randomly selected microscope fields at 200× magnifications under the optical microscope (Nikon) were taken. Results were expressed as the average number of migrated cells at each condition normalized to the average number of migrated cells under 2D culture, in triplicates. Dose-dependent migratory responses of hMSCs to different dosage of Fractalkine (0-80 ng/ml) and SDF-1β (0-400 ng/ml) were studied to determine the sub-optimal concentrations of these chemoattractants before comparing the migratory activities of different MSC subpopulations.

Results

Figure 2A:
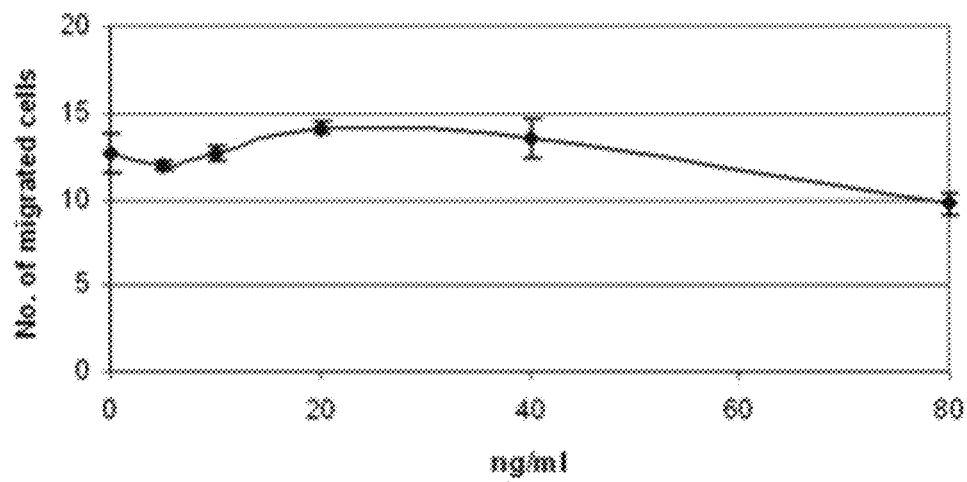
FIGS. 2A and 2B are line graphs showing the dose-dependent (ng/ml) migratory response of 2D cultured hMSCs (number migrated cells) as a function of chemokine concentration (ng/ml) of Fractalkine (FIG. 2A) and SDF-1β (FIG. 2B).
Figure 2B:
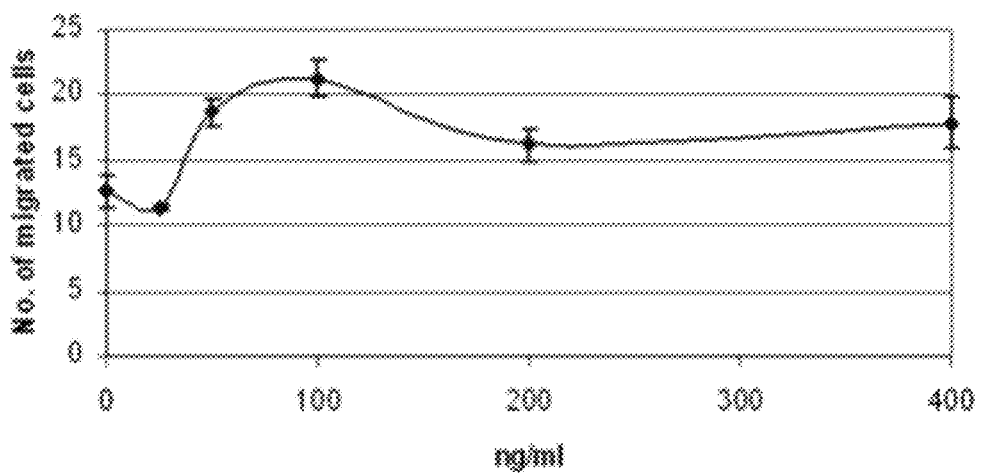
Figure 3A:
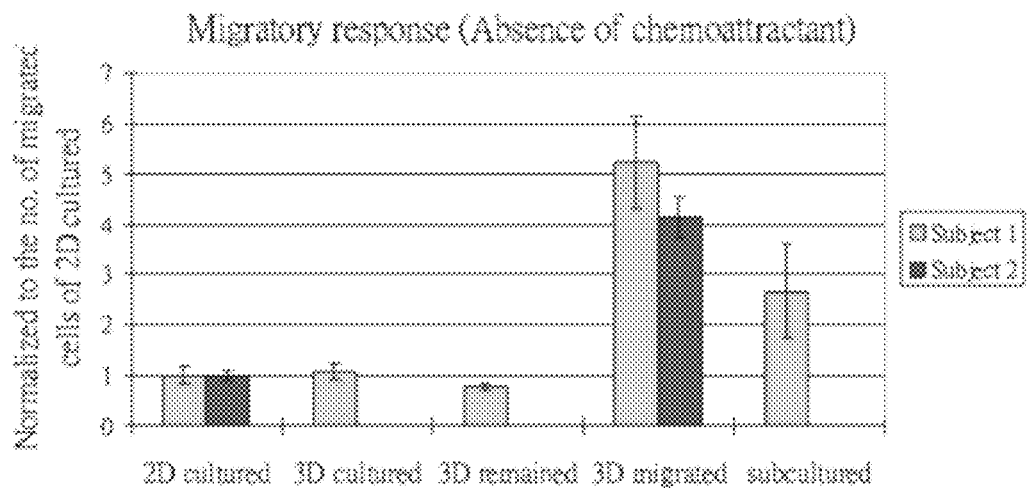
FIGS. 3A, 3B, and 3C are bar graphs showing the relative number (normalized to the number of cells migrating in 2D culture) of 2D cultured hMSCs, 3D cultured hMSCs (cultured in collagen microspheres at free-floating conditions), 3D remained hMSCs (those remaining in microspheres after culture on substratum), 3D migrated hMSCs (those migrating out of microspheres cultured on substratum), and subcultured subpopulations of hMSCs cells from different donors (subject 1 and subject 2) that were migrating spontaneously (no chemoattractant) (FIG. 3A, control), migration towards Fractalkine (FIG. 3B, 10 ng/ml), and migration towards SDF-1 (FIG. 3C, 50 ng/ml).
Figure 3B:
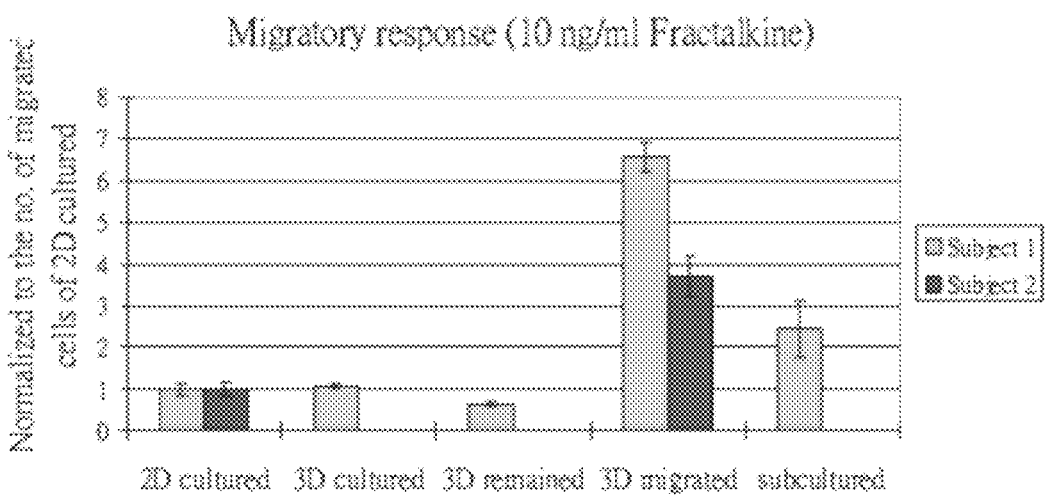
Figure 3C:
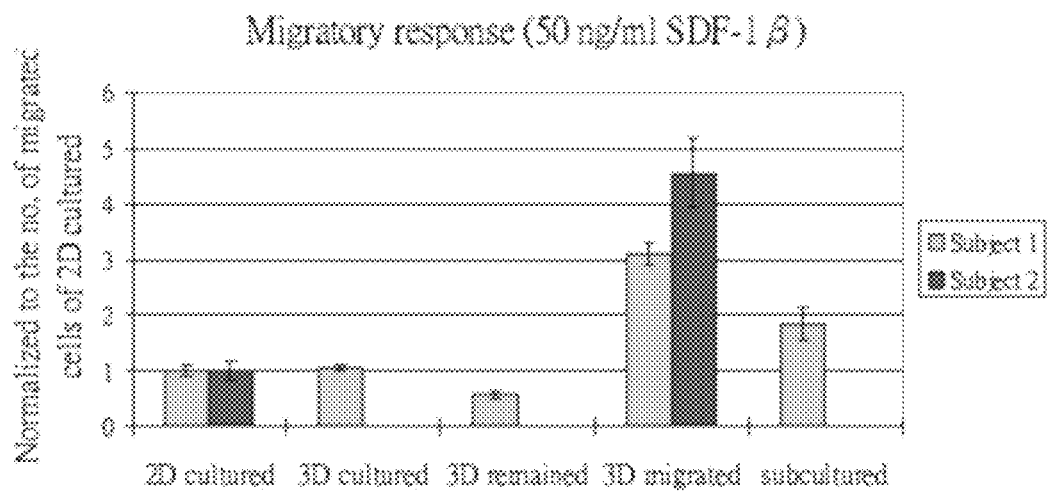
Figure 4:
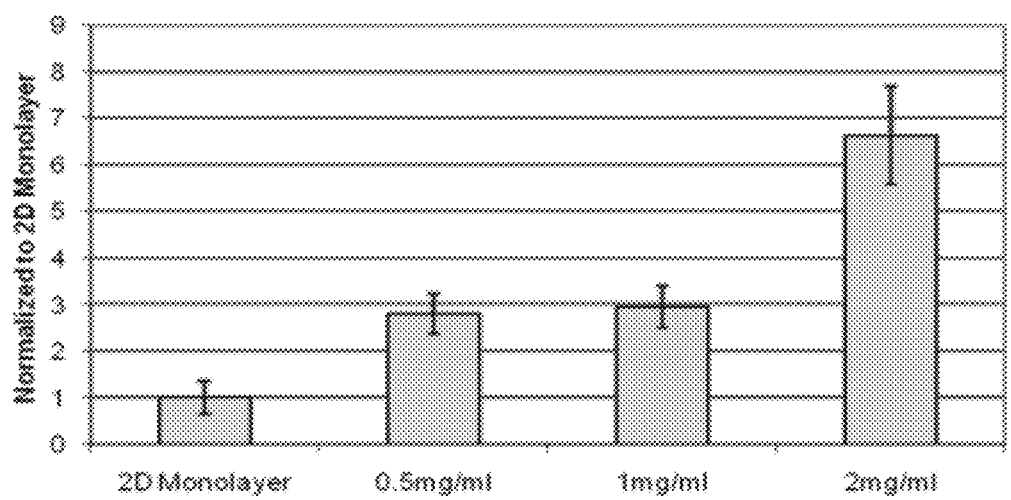
FIG. 4 is a bar graph showing the relative Transwell migratory activity of the 3D migrated hMSC subpopulation from collagen barriers of different collagen concentrations (0, 0.5, 1, and 2 mg/ml) normalized to the Transwell migratory activity of the 2D cultured hMSCs.
Figure 5:
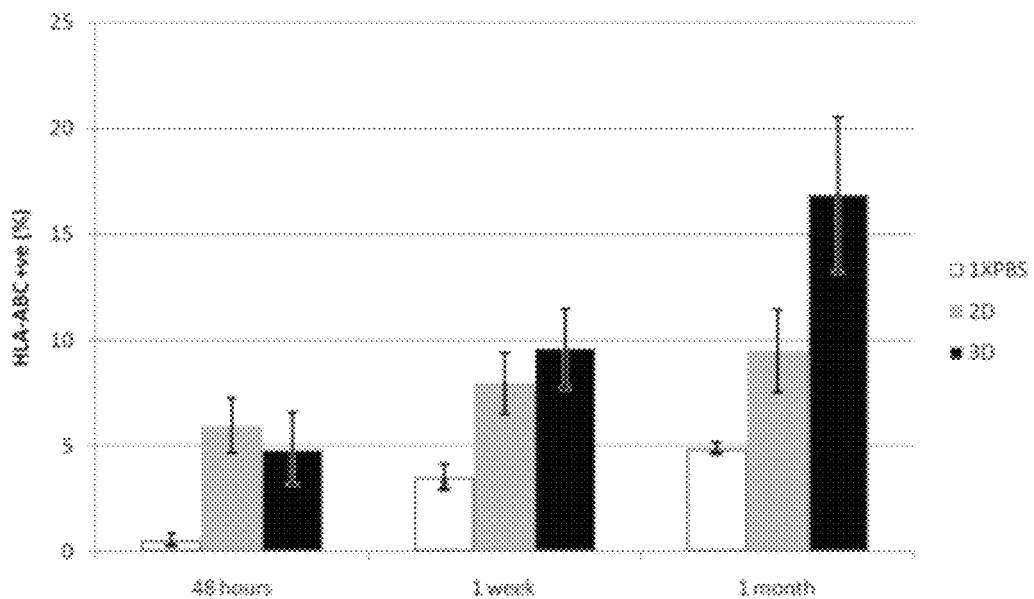
FIG. 5 is a bar graph showing the in vivo engraftment rate (% of liver cells positive for human HLA-ABC) of 3D migrated hMSC subpopulation, 2D cultured hMSCs, and 1×PBS control in partial hepatectomized NOD/SCID mice.

The migratory response of hMSCs is chemokine dose-dependent as shown in FIGS. 2A and 2B for both Fractalkine and SDF-1. FIGS. 3A-3C show the significantly higher migratory activities as shown by the normalized migratory activities in the 3D migrated subpopulation than other subpopulations including the 3D cultured and the 3D remained. FIG. 4 shows the dose-dependent increase in the migratory activities as the collagen barrier concentration increases, indicating that the higher the collagen barrier capacity, the better the migratory activities of the selected population. Therefore, a gradient collagen barrier may select and enrich some MSC subpopulations with super migratory capability.

The temporal morphological change of the cell-matrix microspheres with different cell densities and collagen matrix densities were recorded. Microspheres at day 0 showed individual cells embedding in the collagen matrices and the microspheres were still transparent. Microspheres at higher cell densities such as $1 \times 10^5$ and $5 \times 10^5$ cells/ml and lower collagen matrix densities of 0.5, 1.0 and 2.0 mg/ml contract as time goes by and become more opaque and dense. This indicates that hMSCs are reorganizing the matrix to form a tighter matrix in the microspheres. Microspheres at lower cell density ($2 \times 10^4$ cells/ml) took much more time to contract to a constant size while microspheres with higher collagen matrix density, 3.0 mg/ml, showed so little contraction that the matrix appears transparent. The extent of hMSC-induced collagen microspheres contraction was directly proportional to the cell density, collagen concentration and droplet volume, establishing that that these parameters can be used to control the final size of the microspheres. The hMSC-collagen microspheres, after reaching the equilibrium, can be mechanically manipulated by forceps and are resistant to the shear stress and turbulence generated during pipetting up and down at rapid rate such as 20 ml/min or even vortexed with maximal speed. As a result, these microspheres are mechanically stable enough to resist shear stress generated during microsyringe injection and are ready for injection and implantation for cell therapy and tissue engineering purposes.

Figure 6A:
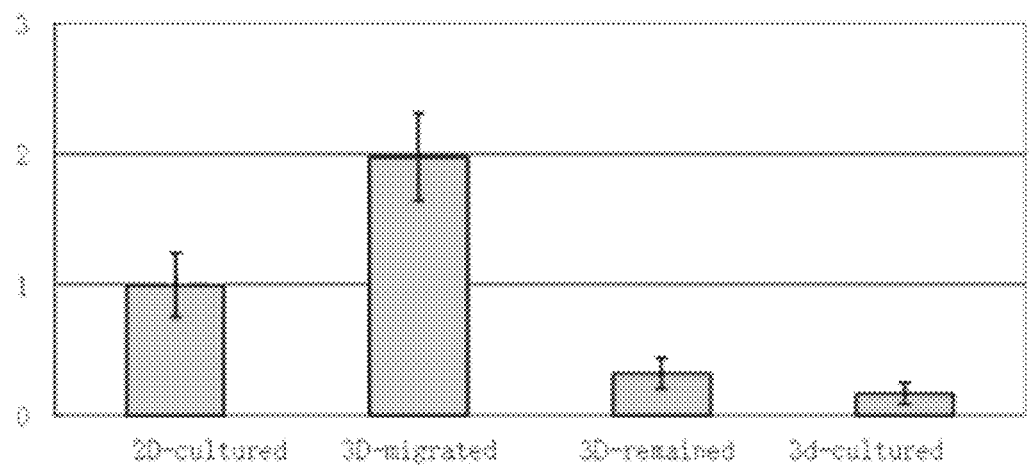
FIGS. 6A, 6B, and 6C are bar graphs showing the relative number (normalized to the number of cells migrating in 2D culture) of 2D cultured hMSCs, 3D cultured hMSCs (cultured in collagen microspheres at free-floating conditions), 3D remained hMSCs (those remaining in microspheres after culture on substratum), 3D migrated hMSCs (those migrating out of microspheres cultured on substratum), and subcultured subpopulations of hMSCs cells from derived from adipose tissue that were migrating spontaneously (no chemoattractant) (FIG. 6A, control), migration towards SDF-1 (FIG. 6B, 50 ng/ml), and migration towards Fractalkine (FIG. 6C, 10 ng/ml).
Figure 6B:
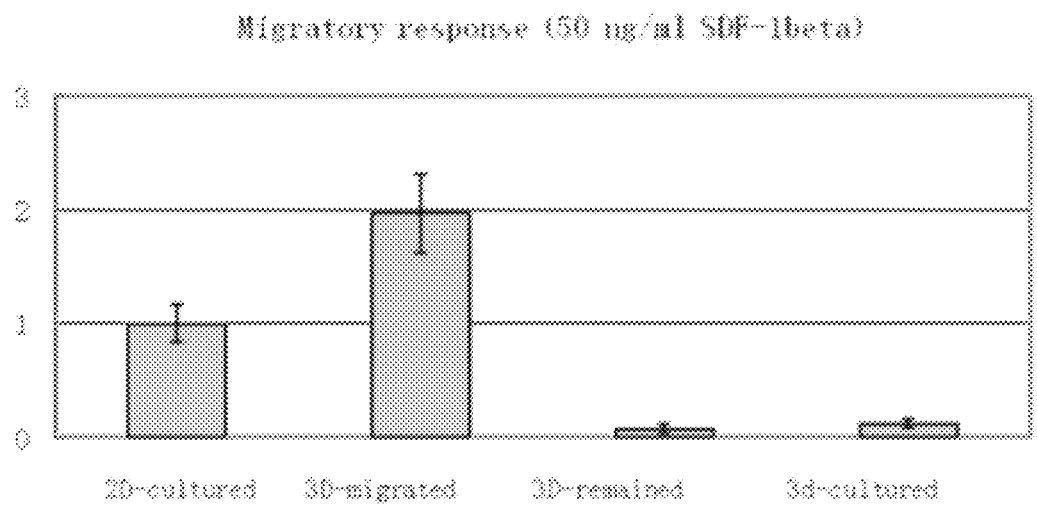
Figure 6C:
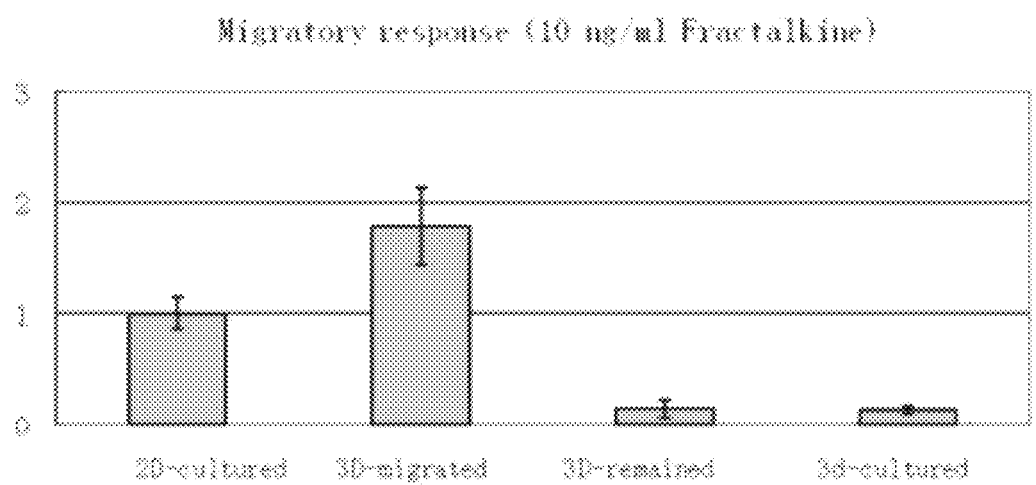
Figure 7:
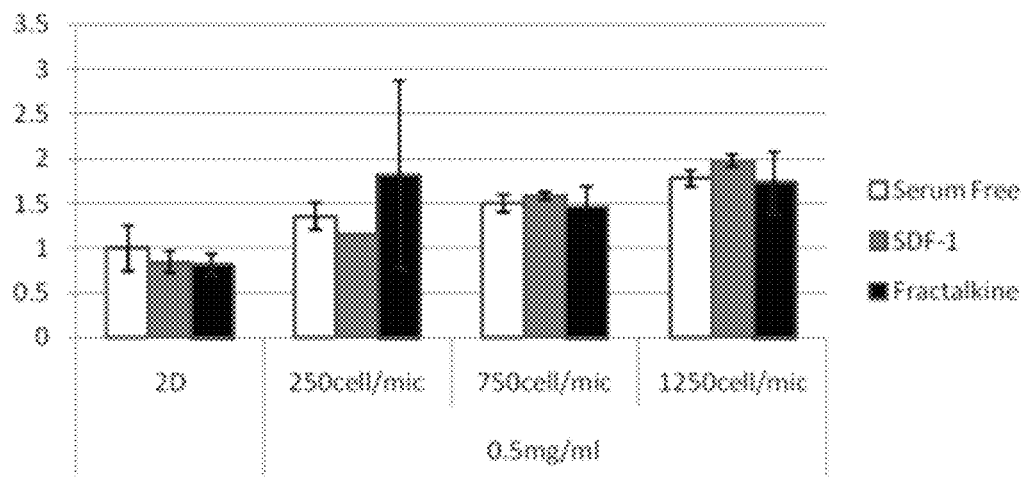
FIG. 7 is a bar graph showing the relative number (normalized to the number of cells migrating in 2D culture) of 3D migrated hMSCs encapsulated in 0.5 mg/ml collagen cultured at a density of 250 cell/µl, 750 cell/µl, or 1250 cell/µl that were migrating spontaneously (no chemoattractant, open bars), migration towards SDF-1 (50 ng/ml, shaded bars), and migration towards Fractalkine (10 ng/ml, solid bars).
Figure 8:
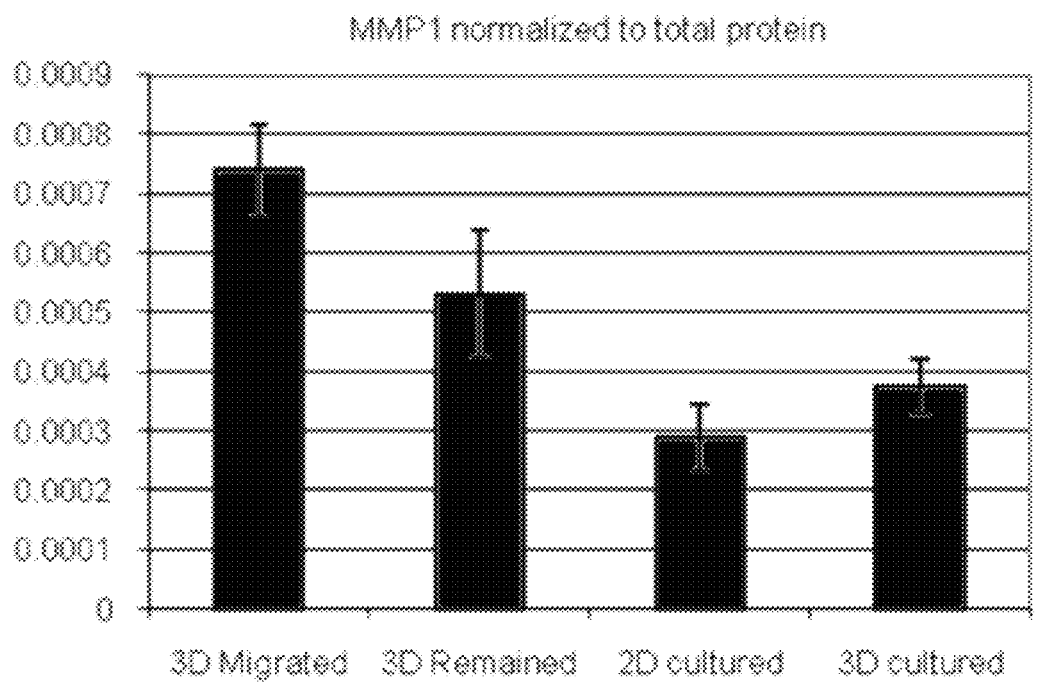
FIG. 8 is a bar graph showing the relative amounts of matrix metalloprotease 1 (MMP1) (normalized to total protein) secreted by 3D migrated hMSCs (those migrating out of microspheres cultured on substratum), 3D remained hMSCs (those remaining in microspheres after culture on substratum), 2D cultured hMSCs, and 3D cultured hMSCs (cultured in collagen microspheres at free-floating conditions).
Figure 9:
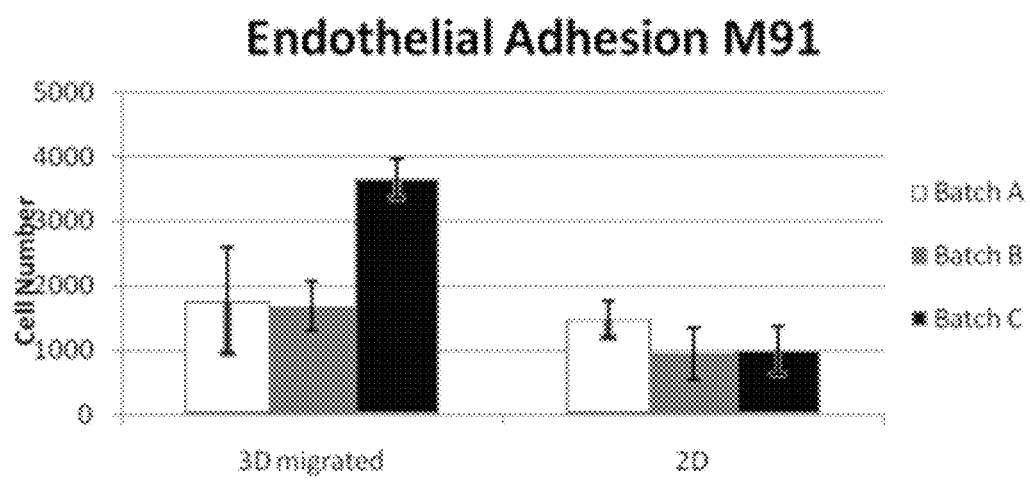
FIG. 9 is a bar graph showing the relative number (normalized to the number of cells migrating in 2D culture) of 2D cultured hMSCs and 3D migrated hMSCs adhering to endothelial cells.

The in vitro migratory activities of the functionally selected (3D migrated) MSCs derived from human adipose tissue were consistent with that from human bone marrow (FIGS. 6A-6C). Functional selection is also cell density dependent. As the cell density increases, the functionally selected cells have better migratory activities (FIG. 7).

In addition, functionally selected MSCs secrete more matrix metalloprotease 1 (MMP1), i.e. collagenase, than other control groups. This further suggests that these functionally selected cells have functional difference, in this case, the ability to digest collagen matrix, comparing with other groups.

Example 3

Engraftment of 3D Migrated Cells in Hepatectomized NOD/SCID Mice

Materials and Methods 8 week old, 25 gram NOD/SCID mice were anesthetized and then the median, left and caudate lobes of the liver, as well as the gall bladder, were removed, leaving the right lobe of liver. Two to three hours were allowed for the mice to recover after the surgery. After that, the mice were anesthetized again. Cell injection was done via the tail vein. Two million migrated cells suspended in 100 μl 1×PBS were used for cell injection.

At 48 hours 1 week and 1 month, mice were sacrificed and the liver collected for human cell marker analysis using flow cytometry and immunohistochemistry. For flow cytometry, cells from the harvested liver were isolated by incubating with collagenase for 20 minutes followed by filtering through the cellular sieve (BD Biosciences). The cell suspension was centrifuged and the supernatant was removed. Blood cells in the cell suspension were lysed by incubating with ACK buffer for 5 minutes. After that, the lysis reaction was stopped by topping up with 1×PBS and centrifuged. Supernatant was removed and the cells were resuspended in 1×PBA. Cells were stained with phycoerythrin (PE) or fluorescein isothiocyanate (FITC)-conjugated mouse monoclonal antibodies (mAbs) according to the instructions provided by the manufacturers. The following mAbs were used in this study: anti-human HLA-ABC (BD Pharmingen™, cat. #555552) and anti-human CD73 (BD Pharmingen™, cat. #550257). The following isotype controls were used in this study: PE-mouse $IgG_{1\kappa}$, (BD Pharmingen™, cat. #555749) and FITC-mouse $IgG_{1\kappa}$, (BD Pharmingen™, cat. #555748). Flow cytometry was done by EPICS Elite ESP high performance cell sorter (Coulter Electronics) and data was analyzed using WinMDI 2.9 software. For immunohistochemistry, samples were fixed in 4% paraformaldehyde at 4° C. overnight. The fixed livers were washed with 1×PBS and dehydrated in increasing concentrations of ethanol ranging from 50% to 100%, then wax embedding and paraffin sectioned (7 μm). Immunohistochemistry of human markers was conducted to determine if there were any human cells in the livers. The samples were blocked by incubating with 10% normal horse serum (NHS) diluted in 1×PBS for 45 minutes at room temperature. The samples were then incubated with primary antibody, beta-2-microglobulin (Santa Cruz, cat. #sc13565) at 1:100 dilution at 4° C. overnight. The samples were incubated with 3% $H_2O_2$ in methanol at room temperature for 30 minutes to block the endogenous peroxidase. The samples were washed with 1×PBS twice followed by incubating with horse anti-mouse secondary antibody at 1:200 dilution at room temperature for 30 minutes. The samples were washed with 1×PBS twice and were incubated with reagent ABC at room temperature for 30 minutes. After that, the samples were washed with 1×PBS twice and were incubated with DAB substrate at room temperature for 5 minutes. Finally, the samples were washed with 1×PBS twice and were counterstained with hematoxylin. The samples underwent dehydration using ethanol ranged from 70% to 100% and then dewaxed using xylene. They were mounted with permanent mounting medium (Depex) with coverslip (Marienfeld).

Results

Flow cytometry analysis showed that the functionally selected hMSCs (3D migrated cells) showed significantly better in vivo engraftment rate in the hepatectomized liver of the NOD/SCID mice particularly at later time point at 1 month as compared with the unprocessed hMSCs (2D cultured cells). Moreover, analysis of the sections showed the engraftment of the 3D migrated hMSCs at 48 hours post-injection based on the immunopositive staining.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method to functionally select a subpopulation of stem cells from a crude preparation of stem cells comprising
   entrapping or encapsulating the crude population of stem cells in a biomaterial barrier or gradient of biomaterial barrier material, and
   selecting the stem cells from the crude preparation of stem cells by allowing the cells to migrate through the barrier or gradient of barrier material and collecting the subpopulation of cells that migrates through the barrier or gradient of barrier material,
   wherein the selected stem cells have an improved engraftment rate compared to the crude preparation of stem cells.

2. The method of claim 1, wherein the crude preparation of stem cells comprise multipotent or pluripotent cells.

3. The method of claim 2, wherein the crude preparation of stem cells comprise stem cells obtained from bone marrow, adipose tissue, umbilical cord blood.

4. The method of claim 3, wherein the crude preparation of stem cells are obtained by adhesion selection or flow cytometry sorting.

5. The method of claim 2, wherein the crude preparation of stem cells are selected from the group consisting of induced pluripotent stem (iPS) cells, embryonic stem (ES) cells, mesenchymal stem cells, or undifferentiated cells derived from the culture of iPS cells, ES cells, mesenchymal stem cells, and a combination thereof.

6. The method of claim 1, wherein the crude preparation of stem cells are mesenchymal stem cells.

7. The method of claim 1, wherein the selected cells are enriched subpopulations of MSCs with enhanced spontaneous migratory activities and directional migration towards chemokines secreted from the circulation during tissue injuries.

8. The method of claim 1, wherein the stem cells are selected from the crude preparation of stem cells that migrate through a barrier or gradient of barrier material in response to a chemoattractant.

9. The method of claim 1, wherein the selected stem cells have an improved migration rate compared to the crude preparation of stem cells.

10. The method of claim 1, wherein the stem cells are selected from the crude preparation of stem cells by allowing the cells to spontaneously migrate through the barrier or gradient of barrier material in the absence of a specific chemoattractant.

11. The method of claim 1, wherein the improved migration ability of the cells is directional and is spontaneous and is independent of presence of chemokines stromal-cell derived factor-1 (SDF-1) or Fractalkine.

12. The method of claim 1, wherein the barrier or gradient of barrier material comprises a biomaterial.

13. The method of claim 12, wherein the biomaterial is selected from the group consisting of collagen, fibrin, extracellular matrix materials, self-assembled peptides, hyaluronic acid, and combinations thereof.

14. The method of claim 1, wherein the barrier or gradient is a homogenous barrier comprising a homogenous fiber density or barrier capacity, or wherein the barrier or gradient is a gradient barrier comprising an increasing fiber density or barrier capacity.

15. The method of claim 1, wherein the barrier is in the form of a microsphere.

16. The method of claim 1, wherein the barrier is selected from the group consisting of a block gel, patch, and thin film.

17. The method of claim 1, wherein the crude population of stem cells are entrapped or encapsulated in the barrier or gradient of barrier material by microencapsulating the cells in solid collagen microspheres.

18. A method to functionally select a subpopulation of stem cells from a crude preparation of stem cells comprising
   entrapping the crude population of stem cells in a barrier or gradient of barrier material,
   culturing the crude population of stem cells entrapped in the barrier or gradient of barrier material in suspension or free floating cultures to allow the cells to adapt to and interact with the environment of the barrier or gradient and the barrier or gradient to contract to an equilibrium status, and
   selecting the stem cells from the crude preparation of stem cells that migrate through the barrier or gradient of barrier material,
   wherein the selected stem cells have an improved engraftment rate compared to the crude preparation of stem cells.

19. The method of claim 18, wherein the entrapped cells are cultured for about 1 to about 14 days.

20. The method of claim 18, wherein the entrapped cells are cultured for about four days.

21. The method of claim 20, further comprising, following culturing the entrapped crude population of stem cells and prior to selecting the stem cells from the crude preparation of stem cells that migrate through a barrier or gradient of barrier material, transferring the entrapped cells into a tissue culture container comprising an adherent surface in the presence of a medium, allowing the entrapped cells to attach to the adherent surface, and culturing the stem cells that migrated out from the barrier or gradient for 1 day to 14 days.

22. The method of claim 21, wherein the medium comprises serum.

23. The method of claim 21, wherein the stem cells that migrated out from the barrier or gradient are selected by detaching the cells from the adherent surface.

24. The method of claim 21, wherein the medium comprises a chemoattractant.

25. A method to functionally select a subpopulation of stem cells from a crude preparation of mesenchymal stem cells comprising entrapping or microencapsulating the crude population of stem cells into solid collagen microspheres, wherein the microspheres comprise a biomaterial barrier or gradient of biomaterial barrier material, and selecting the stem cells from the crude preparation of stem cells that spontaneously migrate through the collagen barrier of the microspheres in the absence of a specific chemoattractant, wherein the selected stem cells have an improved spontaneous migration rate compared to the crude preparation of stem cells.

* * * * *